United States Patent [19]

Hoyle et al.

[11] 4,431,438

[45] Feb. 14, 1984

[54] AMINOETHANE-METHYLPHOSPHINIC ACID DERIVATIVES FOR INFLUENCING PLANT GROWTH

[75] Inventors: William Hoyle, Stockport, England; Rolf Vogel, Reinach, Switzerland

[73] Assignee: Ciba-Geigy Corporation, Ardsley, N.Y.

[21] Appl. No.: 355,181

[22] Filed: Oct. 14, 1980

Related U.S. Application Data

[62] Division of Ser. No. 81,428, Oct. 3, 1979, abandoned.

[30] Foreign Application Priority Data

Oct. 5, 1978 [GB] United Kingdom ............... 39401/78

[51] Int. Cl.³ ............................................. A01N 57/00
[52] U.S. Cl. ........................................... 71/86; 71/76; 71/78; 71/87
[58] Field of Search ........................................ 71/86, 76

[56] References Cited

U.S. PATENT DOCUMENTS

| 3,764,677 | 10/1973 | Kerst et al. | 71/86 |
| 3,920,733 | 11/1975 | Birum | 71/86 |
| 4,016,148 | 4/1977 | Atherton et al. | 424/177 |
| 4,127,649 | 11/1978 | Atherton et al. | 424/177 |
| 4,168,963 | 9/1979 | Rupp et al. | 71/86 |
| 4,205,977 | 6/1980 | Dingwall et al. | 71/86 |
| 4,226,610 | 10/1980 | Takematsu et al. | 71/86 |
| 4,265,654 | 5/1981 | Takematsu et al. | 71/86 |
| 4,309,208 | 1/1982 | Takematsu et al. | 71/86 |

FOREIGN PATENT DOCUMENTS

| 2351124 | 12/1977 | France | 424/177 |
| 2351125 | 12/1977 | France | 424/177 |
| 50-101536 | 1/1975 | Japan | 71/86 |
| 53-127415 | 11/1978 | Japan | 71/86 |
| 1533240 | 11/1978 | United Kingdom | 424/177 |

*Primary Examiner*—Glennon H. Hollrah
*Attorney, Agent, or Firm*—Frederick H. Rabin

[57] ABSTRACT

An agent for influencing plant growth, in particular a herbicidal and plant growth inhibiting agent, contains, in addition to carriers and/or other additives, at least one compound of the formula:

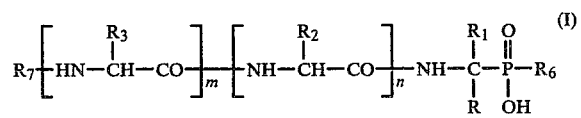

or the corresponding zwitterion form in which R and $R_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above, or R and $R_1$ together form a polymethylene chain optionally interrupted by an oxygen, nitrogen or sulphur atoms, or $R_1$ represents, together with the C(R)—N< residue to which it is attached, the atoms required to complete a heterocyclic radical; and $R_2$ and $R_3$ may be the same or different and each can be hydrogen, optionally substituted lower alkyl, cycloalkyl, aryl or lower alkyl substituted by a heterocyclic radical containing one or more nitrogen atom; a heterocyclic radical containing one or more nitrogen atoms; or $R_2$ and $R_3$, independently, together with the >C(H)—N< residue to which each is attached, may each represent the atoms required to complete a heterocyclic radical; $R_6$ is OH, $CH_3$, or phenyl; $R_7$ is hydrogen or a lower alkoxycarbonyl, cycloalkoxycarbonyl, aryloxycarbonyl or benzyloxycarbonyl group; and m is 0 or 1; n is 0, 1, 2 or 3; as well as the esters or partial esters thereof with physiologically splittable alcohols; salts of the compounds of formula I, or their esters or partial esters with acids or bases physiologically acceptable to plants, respectively; and all optical isomers thereof; provided that when $R_7$ is hydrogen and m and n are each 0, then $R_6$ is not OH.

4 Claims, No Drawings

AMINOETHANE-METHYLPHOSPHINIC ACID DERIVATIVES FOR INFLUENCING PLANT GROWTH

This is a division of application Ser. No. 081,428 filed on Oct. 3, 1979 now abandoned.

The invention relates to a novel agent for influencing plant growth, in particular a herbicidal and plant growth-inhibiting agent, and to a process for inhibiting and suppressing plant growth in monocotyledonous and dicotyledonous plants, especially grasses, cereal crops, soya, tobacco and ornamental plants.

The agent, according to the invention, for influencing plant growth, in particular a herbicidal and plant growth-inhibiting agent, contains, in addition to carriers and/or other additives, at least one compound of the formula I

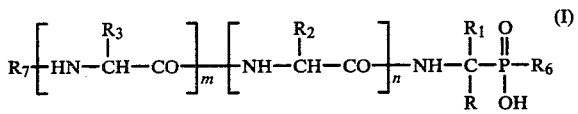

or the corresponding zwitterion form in which R and $R_1$ may be the same or different and each can be hydrogen, deuterium or an optionally substituted lower alkyl group, lower alkenyl, lower alkynyl, cycloalkyl, aryl or heterocyclic radical containing one or more oxygen, nitrogen or sulphur atoms and which may be fused to an aromatic ring, a lower alkyl group substituted by a cycloalkyl radical, a lower alkyl group substituted by an aryl radical, a lower alkyl group substituted by a heterocyclic radical as defined above, or R and $R_1$ together form a polymethylene chain optionally interrupted by an oxygen, nitrogen or sulphur atoms, or $R_1$ represents, together with the

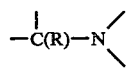

residue to which it is attached, the atoms required to complete a heterocyclic radical; and $R_2$ and $R_3$ may be the same or different and each can be hydrogen, optionally substituted lower alkyl, cycloalkyl, aryl or lower alkyl substituted by a heterocyclic radical containing one or more nitrogen atoms; a heterocyclic radical containing one or more nitrogen atoms; or $R_2$ and $R_3$, independently, together with the $>C(H)-<$ residue to which each is attached, may each represent the atoms required to complete a heterocyclic radical; $R_6$ is OH, $CH_3-$ or phenyl; $R_7$ is hydrogen or a lower alkoxycarbonyl, cycloalkyloxycarbonyl, or aryloxycarbonyl or benzyloxycarbonyl group; and m is 0 or 1; n is 0, 1, 2 or 3; as well as the esters, or partial esters thereof with physiologically splittable alcohols; salts of the compounds of formula I, or their esters, with acids or bases physiologically acceptable to plants, respectively; and all optical isomers thereof; provided that, when $R_7$ is hydrogen and m and n are each 0, $R_6$ is not OH. The α-amino acid residues or esters occurring in the compounds defined above may have the D, L-, L- or D- configuration.

The term "lower" referred to above and hereinafter in connection with organic radicals or compounds respectively, defines such with up to 6, preferably up to 3 carbon atoms.

The above listed radicals R, $R_1$, $R_2$ and $R_3$ optionally may be substituted by one or more functional groups, as for example, free or etherified hydroxy or mercapto groups, optionally converted carboxyl groups, S-substituted dithio groups, optionally substituted amino groups —$NR_4R_5$— in which $R_4$ and $R_5$ may be the same or different and can be hydrogen or lower alkyl or optionally substituted guanidino and/or optionally substituted aryl groups or heterocyclic residues.

Moreover R and $R_1$ as lower alkyl group, aryl group or heterocyclic radical or an aryl group or heterocyclic radical as substituent of R or $R_1$ as lower alkyl group may be substituted by one or more halogen atoms, —$NR_4R_5$ groups in which $R_4$ and $R_5$ together form a polymethylene chain containing up to 6 carbon atoms which may optionally be interrupted by oxygen or nitrogen or an aryloxy group optionally substituted by hydroxy or an halogen atom as for example iodine.

The substituents R, $R_1$, $R_2$ and $R_3$ as lower alkyl group, or the lower alkyl component of alkoxycarbonyl groups $R_7$, may be a straight or branched chain alkyl group of 1 to 6 carbon atoms and may be for example, methyl, ethyl, n-propyl, isopropyl, n-butyl, isobutyl, secondary butyl, tertiary butyl, n-amyl, isoamyl or n-hexyl. Preferred are lower alkyl groups of 1 to 3 carbon atoms as for example methyl, ethyl, n-propyl or isopropyl.

When R, $R_1$, $R_2$ or $R_3$ is a cycloalkyl group or when $R_7$ contains a cycloalkyl component, this may be a cycloalkyl group with 3 to 7 carbon atoms as for example a cyclopropyl, cyclobutyl, cyclopentyl, cyclohexyl or cycloheptyl group.

A lower alkyl group substituted by a cycloalkyl radical may be for example cyclopropyl-methyl, cyclopropyl-ethyl, cyclopropyl-n-propyl, cyclobutyl-methyl, cyclobutyl-ethyl, cyclobutyl-n-propyl, cyclopentyl-methyl, cyclopentyl-ethyl, cyclopentyl-n-propyl, cyclohexyl-methyl, cyclohexyl-ethyl, cyclohexyl-n-propyl, cycloheptyl-methyl, cycloheptyl-ethyl or cycloheptyl-n-propyl.

The term aryl preferably comprises mononuclear groups such as phenyl, which may be substituted in one or more positions by substituents such as lower alkyl, hydroxy, lower alkoxy or halogen.

Moreover in addition to the meaning above when R and $R_1$ or the substituent of a lower alkyl group thereof is an aryl group, this aryl group comprises 6 to 10 carbon atoms and may be for example as mononuclear group a phenyl, tolyl, xylyl, ethylphenyl, propylphenyl, isopropylphenyl, butylphenyl, isobutylphenyl, sec.-butylphenyl, tert.-butylphenyl or naphthyl group.

If the substituents $R_1$, $R_2$ or $R_3$ can also represent together with the

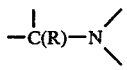

residue, or

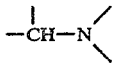

residue respectively, a heterocyclic radical, it is preferably a 5-membered hydrogen-containing ring such as pyrrolidine in proline and 4-hydroxypyrrolidine in hydroxy-proline, and pyroglutamic acid.

A heterocyclic residue as substituent of an optional substituted radical R, $R_1$, $R_2$ and $R_3$ may be a mono- or bicyclic, a monoaza or diazacyclic radical of aromatic character such as imidazolyl, as for example 4-imidazolyl, or indolyl, as for example 3-indolyl radical.

Moreover in addition when R or $R_1$ or the substituent of a lower alkyl group thereof is a heterocyclic ring containing one or more oxygen, nitrogen or sulphur atoms this may be, for example, aziridine, oxetane, thiophene, furan, pyridine, azepine, isoxazole, thiazole, pyrimidine, diazepine, thiadiazol, triazol, triazine, or imidazole or indole as mentioned above.

When R or $R_1$ is a lower alkenyl group this may be a straight or branched chain alkenyl group with 2 to 6 carbon atoms, and may be, for example, an ethenyl, allyl, crotyl, methallyl, pentenyl or hexenyl group.

When R or $R_1$ represents a lower alkynyl group this may be straight or branched chain alkynyl group with 2 to 6 carbon atoms, and may be, for example, an ethynyl, propynyl, butynyl, pentynyl or hexynyl group.

When R and $R_1$ together form a polymethylene chain, comprising a residue of 2 to 7 carbon atoms, this may be for example —$(CH_2)_2$—, —$(CH_2)_3$—, —$(CH_2)_4$—, —$(CH_2)_5$—, —$(CH_2)_6$—, —$(CH_2)_7$—, —$(CH_2)_2CHCH_3(CH_2)_2$— or —$(CH_2)_2NH(CH_2)_2$—.

The term etherified hydroxy is preferably lower alkoxy, such as methoxy, ethoxy, n-propyloxy, isopropyloxy or n-butyloxy and etherified mercapto is preferably lower alklythio as for example methylthio, ethylthio, propylthio or isopropylthio.

The compounds containing S-substituted dithio groups are symmetrical or unsymmetrical residues of a compound of formual I bound to the other residue of a compound of formula I by a S-S-bridge, i.e.

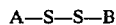

wherein A and B are the same or different and each is a residue of a compound of formual I formed by the loss of a hydrogen atom from a carbon atom in one of the substituents R, $R_1$, $R_2$ or $R_3$.

Examples of such compounds are those having the formulae Ia and Ib

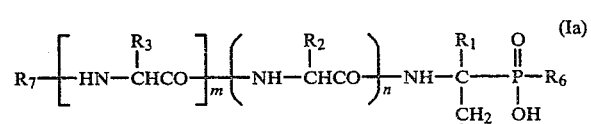

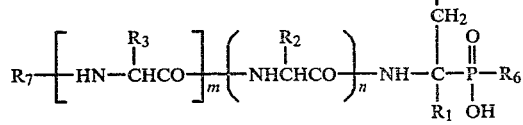

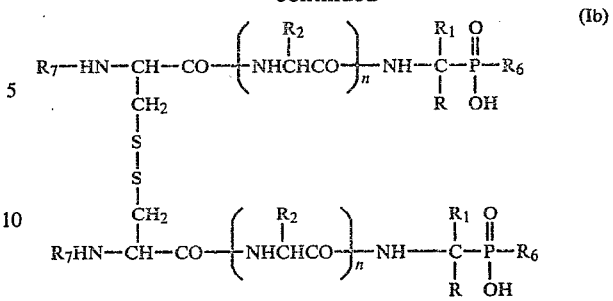

Functionally modified carboxy is, e.g. esterified carboxy, especially lower alkoxycarbonyl, also phenyl-lower-alkoxycarbonyl or carbamoyl.

When R, $R_1$, $R_2$ or $R_3$ is a group substituted by —$NR_4R_5$, in which one or both the $R_4$ and $R_5$ groups are lower alkyl, these groups may be lower alkyl groups as defined above. The —$NR_4R_5$ group including the different meanings enumerated above may be for example, methylamino, dimethylamino, methyl-ethylamino, ethylamino, diethylamino, propylamino, isopropylamino, dipropylamino or diisopropylamino.

The —$NR_4R_5$ groups in which $R_4$ and $R_5$ together form a polymethylene chain containing up to 6 carbon atoms which may optionally be interrupted by oxygen or nitrogen as for instance as substituent of R and $R_1$ and are preferably the morpholino or piperidino group.

Furthermore when R or $R_1$ is a group substituted by an aryloxy, the aryloxy group may be phenoxy, tolyloxy, xylyloxy, diiode- hydroxy phenoxy. $R_7$ as aryloxycarbonyl may be phenyloxycarbonyl, 1-naphthyloxycarbonyl or 2-naphthyloxycarbonyl.

The term halogen may be bromine or iodine but is preferably fluorine or chlorine.

Esters or partial esters of the compounds of formula I are preferably the physiologically splittable esters or partial esters of the compounds of formual I with low alkyl alcohols e.g. methanol, ethanol, n-propanol and n-butanol, aralkyl alcohols e.g. benzyl alcohol and phenols e.g. phenol. Other alcohols which may be used to form the corresponding ester or partial ester of the compound of formula I are alkanoyloxymethanols e.g. acetoxymethanol or pivaloyloxymethanol; amino-lower-alkanoyloxymethanols. e.g. α-amino-lower-alkanoyloxymethanols such as glycyloxy-methanol, L-valyloxymethanol or L-leucyloxymethanols; and also 3-hydroxy-phthalide and 5-indanol.

Salts of the compounds of formula I and the physiologically splittable esters and partial esters are preferably addition salts of the following inorganic or organic acids or bases:

Examples of acids are hydrochloric, hydrobromic, sulphuric, phosphoric, methanesulphonic, ethanedisulphonic, acetic, trichloroacetic, oxalic, succinic, maleic, fumaric, malic, tartaric, citric and mandelic acids: examples of bases are lithium, sodium, potassium, calcium, magnesium, aluminium, iron, ammonium and substituted ammonium, hydroxides and carbonates, and heterocyclic bases.

Particularly useful are compounds of formula I wherein R and $R_1$ may be the same or different and each is hydrogen, deuterium optionally substituted lower alkyl, or lower alkyl substituted by cycloalkyl, aryl or by a mono- or bicyclic monoaza- or diazacyclic radicals, optionally substituted by one to three hydroxy or lower alkoxy groups; or $R^1$ represents, together with the

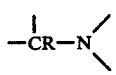

residue to which it is attached, the atoms required to complete a 2-pyrrolidinyl group; $R_2$ and $R_3$ may be the same or different and each is hydrogen, optionally substituted lower alkyl, or lower alkyl substituted by cycloalkyl, aryl, or by a mono- or bicyclic monoaza or diazacylic radical optionally substituted by one to three hydroxy or lower alkoxy groups or $R_2$ and $R_3$ each represents together with the

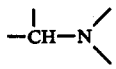

residue to which it is attached, the atoms required to complete the 2-pyrrolidinyl group; $R_6$ is OH or $CH_3$; $R_7$ is hydrogen or lower alkoxycarbonyl, cycloalkyloxycarbonyl, benzyloxycarbonyl or aryloxycarbonyl; m is 0 or 1; and n is 0, 1, 2 or 3; as well as the esters, partial esters and salts with physiologically acceptable alcohols, or acids or bases, respectively; and all optical isomers thereof.

Preferred are compounds of formula I wherein R and $R_1$ may be the same or different and each is hydrogen, deuterium, methyl, ethyl, n-propyl, isopropyl, n-butyl, isobutyl, secondary butyl, tertiary butyl, optionally substituted by imidazolyl, indolyl, benzyl groups optionally substituted by one to three hydroxy groups, lower alkoxy, lower alkylthio, amino or carboxy groups or $R_1$ represents together with the

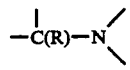

residue to which it is attached, the atoms required to complete a 2-pyrrolidinyl group; $R_2$ and $R_3$ may be the same or different and each can be hydrogen, methyl, isopropyl, isobutyl, benzyl, aminobutyl, hydroxymethyl, 1-hydroxyethyl, 2-methylthioethyl, imidazolylmethyl, or indolylmethyl, or $R_2$ or $R_3$, respectively, together with the

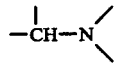

residue to which it is attached, represents the atoms required to complete a 2-pyrrolidinyl group; $R_6$ is OH or $CH_3$; $R_7$ is hydrogen or lower alkoxycarbonyl or benzyloxycarbonyl; m is 0 or 1; and n is 0, 1, 2 or 3; as well as the esters, partial esters and salts with physiologically acceptable alcohols, or acids or bases, respectively; and all optical isomers thereof.

Especially valuable and suitable for said utility are compounds of formula I, wherein R is hydrogen; $R_1$ is methyl, $R_2$ and $R_3$ may be the same or different and each is hydrogen, methyl, isopropyl, isobutyl, aminobutyl, hydroxymethyl, 1-hydroxyethyl, 2-methylthioethyl, imidazolylmethyl or indolylmethyl, benzyl or $R_2$ or $R_3$ respectively together with the

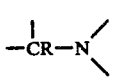

residue to which it is attached represents the atoms required to complete a 2-pyrrolidinyl group; $R_6$ is $CH_3$; $R_7$ is hydrogen, lower alkoxycarbonyl or benzyloxycarbonyl; m is 0 or 1; and n is 0, 1, 2 or 3; and the esters, partial esters and salts thereof with physiologically acceptable alcohols or acids or bases, respectively; and all optical isomers thereof.

Most preferred are compounds of formula I as listed in the following Examples.

Most of the compounds of formual I are described together with processes for their production in U.S. Pat. No. 4,016,148. These compounds of formual I in which $R_6$ is OH can be prepared by the process described in our copending British Patent Application 39399/78 viz. the oxidation of the corresponding compounds in which $R_6$ is H.

The agents according to the invention are prepared in a manner which is in itself known by intimate mixing and grinding of active compounds of the formula I with sutiable carriers, if desired with addition of dispersing agents or solvents which are inert towards the active compounds. The active compounds may exist, and be used, in the following processing forms:

Solid processing forms: dusting agents, sprinkling agents, granules, coated granules, impregnated granules and homogeneous granules;

Active compound concentrates which are dispersible in water: wettable powders, pastes and emulsions:

Liquid processing forms: solutions.

In order to prepare solid processing forms (dusting agents, sprinkling agents and granules), the active compounds are mixed with solid carriers. Examples of carriers which can be used are kaolin, talc, bolus, loess, chalk, limestone, lime grits, attapulgite, dolomite, diatomaceous earth, precipitated silica, alkaline earth metal silicates, sodium and potassium aluminosilicates (feldspars and micas), calcium and magnesium sulphates, magnesium oxide, ground plastics, fertilizers, such as ammonium sulphate, ammonium phosphate, ammonium nitrate and urea, ground vegetable products, such as cereal flour, bark flour, wood flour, nutshell flour, cellulose powder, plant extract residues, active charcoal and the like, in each case on their own or as mixtures with one another.

Granules can be prepared by, for example, dissolving the active compounds in an organic solvent, applying the solution thus obtained to a granulated material, for example attapulgite, $SiO_2$, granicalcium or bentonite, and then again evaporating the organic solvent.

It is also possible to prepare polymer granules by, for example, impregnating finished, porous polymer granules such as urea/formaldehyde polymers, polyacrylonitrile and polyesters, having a specific surface area and an advantageous predetermined absorption/desorption ratio, with the active compounds, for example in the form of their solutions (in a low-boiling solvent) and removing the solvent. Such polymer granules can be applied in the form of micro-granules with bulk densities of, preferably, 300 g/liter to 600 g/liter, also with the aid of atomisers, Atomising can be effected over extensive treatment areas by means of aircraft.

Granules can also be obtained by compacting the carrier with the active compounds and additives and then comminuting the mixture.

Furthermore, it is possible to add to these agents additives which stabilise the active compound and/or nonionic, anionic and cationic materials which, for example, improve the adhesion of the active compounds to plants and parts of plants (adhesives and glues) and/or ensure better wettability (wetting agents) and dispersibility (dispersing agents). It is possible to use, for example, the following materials as adhesives: olein/lime mixture, cellulose derivatives (methylcellulose and carboxymethylcellulose), hydroxyethylene glycol ethers of monoalkylphenols and dialkylphenols having 5 to 15 ethylene oxide residues permolecule and 8 to 9 carbon atoms in the alkyl radical, ligninsulphonic acid, its alkali metal salts and alkaline earth metal salts, polyethylene glycol ethers (Carbowaxes), fatty alcohol polyglycol ethers having 5 to 20 ethylene oxides residues per molecule and 8 to 18 carbon atoms in the fatty alcohol part, condensation products of ethylene oxide and propylene oxide, polyvinylpyrrolidones, polyvinyl alcohols, condensation products of urea/formaldehyde and latex products.

Water-dispersible active compound concentrates, i.e. wettable powders, pastes and emulsion concentrates, are agents which can be diluted with water to any desired concentration. They consist of active compound, carrier, if desired additives which stabilise the active compound, surface-active substances and anti-foaming agents and, if desired, solvents.

The wettable powders and pastes are obtained by mixing and grinding the active compounds with dispersing agents and pulverulent carriers in suitable devices until homogeneity is achieved. Examples of carriers are those mentioned above for the solid processing forms. In some cases it is advantageous to use mixtures of different carriers.

Examples of dispersing agents which can be used are: condensation products of sulphonated naphthalene and sulphonated naphthalene derivatives with formaldehyde, condensation products of naphthalene or of naphthalenesulphonic acids with phenol and formaldehyde, and alkali metal salts, ammonium salts and alkaline earth metal salts of ligninsulphonic acid, as well as alkylarylsulphonates, alkali metal salts and alkaline earth metal salts of dibutylnaphthalenesulphonic acid, fatty alcohol sulphates, such as salts of sulphated hexadecanols and heptadecanols, and salts of sulphated fatty alcohol polyethylene glycol ethers, the sodium salt of oleyl methyl tauride, di-tertiary acetylene glycols, dialkyldilaurylammonium chloride and alkali metal salts and alkaline earth metal salts of fatty acids.

Examples of anti-foaming agents which can be used are silicones.

The active compounds are mixed, ground, sieved and strained with the abovementioned additives, in such a way that the particle size of the solid component does not exceed 0.02 to 0.04 mm in the case of wettable powders and 0.03 mm in the case of pastes. To prepare emulsion concentrates and pates, dispersing agents, such as have been listed in the preceeding sections, organic solvents and water are used. Examples of suitable solvents are the following: alcohols, benzene xylenes, toluene, dimethylsulphoxide, N,N-di-alkylated amides and trialkylamines. The solvents must be virtually odourless and inert towards the active compounds and should not be readily combustible.

Furthermore, the agents according to the invention can be in the form of solutions. For this purpose, the active compound or several active compounds of the formula I is/are dissolved in suitable organic solvents, solvent mixtures, water or mixtures of organic solvents with water.

The content of active compound in the agents described above is between 0.1 and 95%, preferably between 1 and 80%.

Use forms can be diluted down to 0.001%. The amounts used are as a rule 0.1 to 10 kg of active substance/hectare, preferably 0.25 to 5 kg of active substance/hectare. The active compounds of the formula I can be formulated, for example, as follows (parts are parts by weight):

Dusting agents:

The following substances are used for the preparation of (a) a 5% strength dusting agent and (b) a 2% strength dusting agent:

(a) 5 parts of (IR)-1-(L-alanylamino)-ethanephosphonic acid and 95 parts of talc, (b) 2 parts of [(L-alanylamino)methyl]-methylphosphinic acid, 1 part of highly disperse silica and 97 parts of talc.

The active compounds are mixed and ground with the carriers.

Granules:

The following substances are used for the preparation of 5% granules.

5 parts of (IRS)-1-(L-alanylamino)-ethanephosphonic acid,
0.25 part of epichlorohydrin,
0.25 part of cetylpolyethylene glycol ether containing 8 moles of ethylene oxide,
3.50 parts of polyethylene glycol and
91 parts of kaolin (particle size 0.3 to 0.8 mm).

The active substance is mixed with the epichlorohydrin and dissolved in acetone, after which polyethylene glycol and cetyl polyethylene glycol ether are added. The solution thus obtained is sprayed onto kaolin and the acetone is subsequently evaporated off in vacuo.

Wettable powders:

The following constituents are used for the preparation of (a) a 50% strength wettable powder, (b) a 25% strength wettable powder and (c) a 10% strength wettable powder:

(a)
50 parts of (1R)-1-(L-alanyl-L-alanyl-L-alanylamino)-ethanephosphonic acid,
5 parts of sodium dibutylnaphthylsulphonate,
3 parts of a naphthalenesulphonic acid/phenolsulphonic acids/formaldehyde condensate, 3:2:1,
20 parts of kaolin and
22 parts of Champagne chalk;

(b)
25 parts of the diethanolamine salt of the above active compound,
5 parts of the sodium salt of oleyl methyl tauride,
2.5 parts of a naphthalenesulphonic acids/formaldehyde condensate,
0.5 part of carboxymethylcellulose,
5 parts of neutral potassium aluminium silicate and 62 parts of kaolin;
(c)
10 parts of (1R)-1-(L-alanylamino)-ethanephosphonic acid,
3 parts of a mixture of the sodium salts of saturated fatty alcohol sulphates,
5 parts of a naphthalenesulphonic acids/formaldehyde condensate and
82 parts of kaolin.

The active compound indicated is absorbed onto the appropriate carriers (kaolin and chalk) and is then mixed and ground. Wettable powders of excellent wettability and suspensibility are obtained. Suspensions of any desired active compound concentration can be obtained from such wettable powders by dilution with water. Suspensions of this type are used for combating weeds and wild grasses in crops of plants by the pre-emergence process, and for the treatment of lawns.

Paste:

The following substances are used for the preparation of a 45% strength paste:
45 parts of (1R)-1-(L-alanyl-L-alanyl-L-alanylamino)-ethanephosphonic acid,
5 parts of sodium aluminium silicate,
14 parts of cetyl polyethylene glycol ether containing 8 mols of ethylene oxide,
1 part of oleyl polyethylene glycol ether containing 5 mols of ethylene oxide,
2 parts of spindle oil,
23 parts of water and
10 parts of polyethylene glycol.

The active compound is intimately mixed and ground with the additives in apparatus which is suitable for this purpose. A paste is obtained, from which suspensions of any desired concentration can be prepared by dilution with water. The suspensions are suitable for the treatment of lawns.

Emulsion concentrate:

For the preparation of a 25% strength emulsion concentrate,
25 parts of (1RS)-1-(L-alanylamino)-ethanephosphonic acid,
5 parts of a mixture of nonylphenol polyoxyethylene and calcium dodecylbenzenesulphonate,
35 parts of 3,5,5-trimethyl-2-cyclohexen-1-one and
35 parts of dimethylformamide are mixed with one another. This concentrate can be diluted with water to give emulsions of suitable concentrations.

Instead of the particular active compound indicated in the above formulation examples, it is also possible to use other compounds from amongst those included in the formula I.

The active compounds contained in the agents according to the invention influence the plant growth in various ways. Thus they inhibit, delay or suppress, in particular, the growth and germination. They therefore have a post-emergent herbicidal action as well as a growth inhibiting action.

Agents according to the invention, which contain at least one compound of the formula I as the active component, are suitable, in particular, for inhibiting and suppressing plant growth in monocotyledonous and dicotyledonous plants by post-emergent treatment of the sown areas or of the plants, such as shrubs, trees, leguminous crops, sugar cane, onion and potato tubers, fruit trees and vines and, in particular, grasses, cereal crops, tobacco, soya and ornamental plants.

The action achieved, in particular, by the active compounds of the formula I is the desired reduction in plant size, especially the height of growth. In general, a certain change in the form of the plant is associated with this. In direct association with the reduction of the height of growth, the plant is strengthened. The leaves and stem develop more strongly. The resistance to kinking of monocotyledonous plants in increased by shortening the internodal distances. Crop losses due to a thunderstorm, continuous rain and the like, which usually lead to lodging of cereal crops and leguminous crops, can be largely prevented in this manner and harvesting can thus be made easier. As a side effect, reduced height of growth of useful plants leads to a saving of fertilisers. This also applies, in the same way, to ornamental plants, ornamental lawns, sports fields or other grassed areas.

However, one of the most important problems of pure grass plantings is the actual cutting of the grass, whether in public parks in urban areas, on industrial sites, on playing fields or alongside motor-roads, aircraft landing strips, railway embankments or the sloping banks of waterways. In all these cases it is necessary to mow the lawn or cut the growth of grass periodically. This is not only very expensive in terms of labour and machinery, but, in the transport sector, also involves considerable dangers for the personal concerned and for the occupants of vehicles.

There is therefore, particularly in areas with large traffic networks, an urgent need on the one hand to maintain and care for the greensward which is necessary to strengthen road verges and embankments on traffic routes and, on the other hand, to keep it at a medium height of growth during the whole vegetation period, using simple measures. This need is met in a very favourable manner by applying active compounds of the formula I.

By treating trees, shrubs and hedges, in particular in urban and industrial areas, with compounds of the formula I, the labour-intensive mowing work can be reduced in an analogous manner.

The growth of shoots and/or the fertility of fruit trees and vines can also be advantageously influenced by using the active compounds of the formula I.

Ornamental plants with pronounced longitudinal growth can be grown as compact pot plants by treatment with the active compounds mentioned.

The active compounds of the formula I are also used for inhibiting the growth of undesired side shoots, for example in tobacco and ornamental plants, whereby the labour-intensive manual breaking off of these shoots is avoided, and furthermore for the inhibition of sprouting in the case of stored tubers, for example in the case of tubers of ornamental plants and in the case of onions and potatoes, and finally for increasing the yield in the case of crop plants having an intensive vegetative growth, such as soya and sugar cane, by accelerating the transition from the vegetative growth phase to the generative growth phase through application of active compounds of the formula I.

The active compounds of the formula I are preferably employed for inhibiting the growth of weeds, especially perennial weeds, of grasses, especially perennial grasses, such as Cyperus species and the like, and of cereal crops, tobacco, soya and ornamental plants.

The amounts used vary and depend on the time of application. In general, they are between 0.1 and 5 kg of active compound per hectare for the treatment of existing crops, preferably up to 4 kg per hectare.

The action of the active compounds according to the definition is directed towards the parts of the plant which are above ground (contact action), in particular the leaves.

The action as a powerful growth inhibitor is shown by the fact that most of the species of plants treated in a post-emergent manner stop growing after an experimental period of three weeks, the parts of the plant treated assuming a darkgreen coloration. However, the leaves do not fall.

In the case of some species of plants, this growth inhibition already occurs at a dosage of 0.5 kg/hectare and less.

Since not all species of plants are equally powerfully inhibited, it is possible to use the active compounds selectively when a particular low dosage is chosen.

The active compounds of the formula I are also interesting combination partners for a number of herbicides of the diphenyl ether, phenylurea and triazine series for use on cereal crops, maize and sugar cane and in fruit growing and viticulture.

In areas with an increased danger of erosion, the active compounds of the formula I can be used as growth inhibitors on the most diverse crops.

In this case, the weed cover is not removed but only inhibited to such an extent that it can no longer compete with the crop plants.

The following Examples further illustrate the present invention.

USE EXAMPLE 1

The following test methods were used to demonstrate the usefulness of the active compounds as herbicides (post-emergent) and as growth inhibitors:

POST-EMERGENT HERBICIDAL ACTION (CONTACT HERBICIDE)

The plants of 6 weeds and crop plants, both monocotyledonous and dicotyledonous, were sprayed after emergence (in the 4-leaf to 6-leaf stage) with an aqueous active compound emulsion in a dosage of 4 kg of active substance per hectare, and the plants were kept at 24°–26° C. and a relative atmospheric humidity of 45°–60°%. The test was evaluated 5 days and 15 days after treatment and the result is given in the following Table I.

TABLE 1

| | Post Emergent Herbicidal Action | | | | | |
|---|---|---|---|---|---|---|
| | Plant | | | | | |
| Compound | Avena sativa | Setaria italica | Lolium perenne | Solanum lyco-persicum | Sinap-is alba | Stellaria media |
| $CH_3 \quad CH_3$<br>$\| \quad \|$<br>$H_2NCHCONHCHPO_3H_2$<br>L $\quad$ R | 6 | 6 | 6 | 3 | 8 | 6 |

9 = plants undamaged (as untreated control)
1 = plants completely dead
8—2 = intermediate stages of damage.

The results demonstrate that the compounds according to the present invention which were tested exhibited a pronounced contact herbicidal action on some plants and, as a symptom of the growth inhibiting properties, halted the growth of many plants.

Growth inhibition in grasses

Seeds of the grasses *Lolium perenne, Poa pratensis, Festuca ovina* and *Dactylis glomerata* were sown in plastic bowls containing an earth/peat/sand mixture (6:3:1) and were watered normally. Every week the emergent grasses were cut back to a height of 4 cm and, 40 days after being sown and 1 day after the last cutting, were sprayed with aqueous spray liquors of an active compound of the formula I. The amount of active compound corresponded to 5 kg of active substance per hectare. The growth of the grasses was evaluated 10 and 21 days after application.

Growth inhibition in cereals

Spring wheat (*Triticum aestivum*), spring barley (*Hordeum vulgare*) and rye (*Secale*) were sown in sterilised earth in plastic beakers and the plants were grown in a greenhouse. 5 days after being sown, the cereal shoots were treated with a spray liquor of the active compound. The application to the leaves corresponded to 6 kg of active compound per hectare. Evaluation is carried out after 21 days.

The active compounds of the formula I cause a noticeable inhibition of growth both in the case of the grasses and in the case of the cereals. Extraordinary activity in cereals was observed with the compounds of Examples No. 10 and 11.

Growth inhibition of side shoots of tobacco plants

Eight weeks after sowing, tobacco *Nicotina tabacum* (variety Xanthi) are transplanted to pots in a greenhouse, normally watered and treated weekly with nutrient solution. Two weeks after potting, there are chosen per treatment three plants; of these plants one remains untopped and from the two others the growth tip is removed five days before treatment.

Per plant there is then sprayed, laterally from above onto the leading shoot and the upper leaf axils, 10 ml of liquor containing active substance (concentrations: 2.6; 1.3 and 0.6% corresponding to 6.3 and 1.5 kg per hectare in the open). A part of the liquor consequently runs down the petioles and into the remaining lower leaf axils (contact with side-shoot buds).

After setting up of the tests in the greenhouse and watering, the tests are evaluated 4 and 14 days after application of the test liquor.

Contact effect and systemic effect are evaluated separately. Contact effect: Assessment of the 6 uppermost side shoots: Systemic effect: Assessment of the uppermost side shoots.

Good results are obtained in these tests with the compounds of formula I especially with the compound of Example 10.

The preparation of some active compounds of the formula I which can be used according to the invention is described in the following preparative Examples.

EXAMPLE 2

DL-1-Aminoethanephosphonous acid (0.018M), mercuric chloride (0.036 M) and water (50 ml) were mixed and heated to reflux for 1 hour. The white insoluble mercurous chloride which formed was removed by filtration and the aqueous filtrate was evaporated to dryness. The oily residue was dissolved in ethanol (20 ml) and propylene oxide was added until precipitation was complete. Filtration gave D L-1-aminoethanephosphonic acid having m.p. 275°–277°. Mixed m.p. with authentic specimen 275°–277°.

EXAMPLE 3

The method described in Example 2 was repeated using 1R-1-(L-alanylamino)-ethanephosphonous acid (0.034 M), mercuric chloride (0.068 M) and water (175 ml) to give 1R-1-(L-alanylamino)-ethane-phosphonic acid which was recrystallised from ethanol/water m.p. 293°–5°, $[\alpha]_D^{20} -49.3°$ (1%,H$_2$O).

EXAMPLE 4

The method described in Example 2 was repeated using (S-1-(L-alanylamino)-ethanephosphonous acid (0.0048 M), mercuric chloride (0.00096 M) and water (25 ml) to give 1S-1-(L-alanylamino)-ethane-phosphonic acid which was recrystallised from ethanol/water, m.p. 290°–2°$[\alpha]_D^{20} +71.6°$ (1%,H$_2$O).

EXAMPLE 5

The method described in Example 2 was repeated using 1R-1-(L-alanyl-L-alanyl-L-alanyl-alanylamino)-ethanephosphonous acid (0.003 M), mercuric chloride (0.006 M) and water (25 ml) to give 1R-1-(L-alanyl-L-alanyl-L-alanylamino)-ethanephosphonic acid m.p. 307°–8° decomp. $[\alpha]_D^{20} -100°$ (0.5% in 1 M NaOH).

EXAMPLE 6

(a) Aminodiphenylmethane (18.3 g.) and isobutyraldehyde (7.2 g) were refluxed in cyclohexane, removing water (1.8 ml) by means of a Dean and Stark apparatus over two hours. The cyclohexane was removed under vacuum and the resulting Schiff base was dissolved in dioxan (200 ml). To this cooled solution (10°) was added methyldichlorophosphine (11.7 g.) and acetic acid (22.0 g.) and the mixture was stirred for 12 hours. Water (50 ml) was added and the mixture evaporated to dryness. The viscous oil which remained was heated with 50% aqueous HBr for 4 hours at 100° C. and then the mixture was evaporated to dryness and washed with ether. The residue was dissolved in ethanol and propylene oxide was added and the mixture again evaporated to dryness. Trituration with acetone gave (DL-1-amino-2-methylpropyl)-methyl-phosphinic acid mp. 242° decomp. (1.5 g.)

(b) (DL-1-amino-2-methylpropyl)-methylphosphinic acid (0.1 g., 0.0066 M) in water (38 ml) and ethanol (19 ml) was cooled to 10° and sodium bicarbonate (1.11 g., 0.0132 M) was added. To this mixture at 0° was added a solution of the N-hydroxy-succinimide ester of N-benzyloxycarbonyl-L-alanine (2.1 g., 0.0066 M) in hot ethanol (26 ml) over 10 minutes maintaining the internal temperature at 0°.

The mixture was stirred for 2 hours at 0° and a further 24 hours at room temperature. The resulting clear solution was evaporated to dryness to give a viscous gum. Treatment of this residue with cold dilute hydrochlorid acid (2 N.50 ml) gave a mixture of the diastereomers of {1-[(N-benzyloxycarbonyl-L-alanyl)-amino]-2-methylpropyl}-methylphosphinic acid.

This mixture of diastereomers was stirred with a solution of hydrogen bromide in glacial acetic acid (20 ml 45% w/w) at 0° for 30 minutes and at room temperature for 1 hour. The mixture was evaporated to dryness and the residue was disolved in ethanol (10 ml). Propylene oxide (1 ml) was added until precipitation was complete. There was obtained by filtration a mixture of the diastereomers of [1-(L-alanylamino)-2-methylpropyl]-methylphosphinic acid.

EXAMPLE 7

DL-1-Aminoethane-methylphosphinic acid (9.3 g, 0.075 M) was dissolved in water (375 ml) and ethanol (190 ml) and the solution was cooled to 10°. Sodium bicarbonate (12.75 g. 0.15 M), was added portionwise with stirring and the resulting solution was cooled to 0°.

A solution of the N-hydroxysuccinimide ester of N-benzyloxycarbonyl-L-alanine (24.0 g, 0.075 M) in hot ethanol (260 ml) was added over a period of 15 minutes maintaining the internal temperature at 0°.

The heterogeneous mixture was stirred 2 hours at 0° and then 24 hours at room temperature. The clear solution was evaporated at room temperature to give a resinous residue. Treatment of this residue with cold dilute hydrochloric acid (2 N, 150 ml) gave after 2 hours at room temperature no residue. Therefore the solution was evaporated to give an amorphous powder (19.5 g) which was homogeneous in a thin layer chromatogramm solvent system and different to the educts. This residue of 1-[(N-benzyloxycarbonyl-L-alanyl)amino]-ethane-methylphosphinic acid was added to a solution of hydrogen bromide in glacial acetic acid (50 ml, 45%, w/w) at 0° and the mixture was stirred for thirty minutes. The solution was allowed to warm up to room temperature and then evaporated to an oily residue. This residue was dissolved in dry methanol (60 ml) and propylene oxide was carefully added with cooling. There was no crystallisation after two hours stirring at room temperature and standing at 0° for twelve hours. So the solution was evaporated to give an amorphous powder (15.3 g). The TL-chromatogram showed impurities of of hydrolysed and protected educts. A water solution of the raw material was eluted though a Sephadex LH-20 column with water, which gave a partial separation of pure 1-(L-alanylamino)-ethanemethylphosphinic acid (2,4 g, m.p. (90°) 123°–25° C. with decomposition).

EXAMPLES 8 to 18

Analogously to these examples, the following compounds were prepared:
8. DL-(1-aminoethane)-phenylphosphinic acid m.p.>250°.
9. ]1-(N-benzyloxycarbonyl-glycylamino)ethane]-methylphosphinic acid m.p. 92°–95° (amorphous).
10. (1-aminoethane)-methylphosphinic acid m.p. 236°–240°.
11. (L-alanylamino)methyl-phosphonic acid m.p. 152° (decomposition)
12. (aminomethyl)-methylphosphinic acid m.p. 275°–276°.
13. (1-aminobenzyl)-methylphosphinic acid m.p. 273°.

14. (1-glycylaminoethane)-methylphosphinic acid m.p. 140°–143°.
15. (1-aminoethane)-phosphonic acid monomethyl ester m.p. 235°.
16. 1-RS-1-(N-benzyloxycarbonylamino)ethanephosphonic acid m.p. 110°–112°.
17. 1-R-1-[(N-benzyloxycarbonyl-L-alanyl)-amino]ethanephosphonic acid m.p. 171°–171.5°.
18. 1-RS-1-[(N-benzyloxycarbonyl-L-alanyl)aminoethanephosp onic acid m.p. 148°–150°.

EXAMPLE 19

1R-1[(N-Benzyloxycarbonyl-L-alanyl)-amino]-ethanephosphonous acid (0.01 M), mercuric chloride (0.03 M), sodium bicarbonate (0.03 M) and water (25 ml) were mixed and stirred at 20° C. for one hour and then at 90°–95° C. for a further 1½ hour. The mixture was cooled and filtered. The filtrate was acidified with 2N hydrochloric acid and extracted with ethyl acetate (3×100 ml). The extract was dried over magnesium sulfate and evaporated to dryness to give 1R-1-[(N-benzyloxycarbonyl-L-alanyl)-amine]ethanephosphonic acid, m.p. 171°–171.5° C., $[\alpha]_D^{22} - 30.5°$ (2% ethanol). The yield was 58% of the theory.

1.5 g of the above product, 0.8 g of trichloroacetonitrile, 1 g of dry methanol and 14.7 ml of pyridine were stirred together at 100° C. for 4 hours. Then, 10 ml of saturated aqueous sodium bicarbonate solution were added and the resulting yellow solution evaporated to about half its original volume. The precipitated trichloroacetamide was then removed by filtration. The filtrate was acidified to pH 1 with 6N hydrochloric acid and extracted 3 times with 50 ml of ethyl acetate. The combined extracts were dried over magnesium sulfate and evaporated to dryness to give, after washing with ether the methyl ester of 1R-1-[(N-benzyloxycarbonyl-L-alanyl) amino] ethane phosphonic acid with a melting point of 159° C., $[\alpha]_D^{22} - 35.25°$ (2% ethanol). The yield was 53% of the theory.

Two grams of this product, 100 ml of methanol and 0.5 g of a 5% palladium on charcoal-catalyst were shaken with hydrogen at a pressure of 15 pounds per square inch for 3 hours at 20° C. The catalyst was filtered off, the filtrate evaporated and the residue treated with ether to give the methyl ester of 1R-L-alanylaminoethane phosphonic acid as white hygroscopic powder.

What we claim is:

1. A method for combating weeds and inhibiting the growth of plants which comprises applying to the plant a herbicidally or growth-inhibiting effective amount of (1-aminoethane)-methylphosphinic acid of the formula

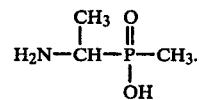

2. A method as claimed in claim 1 wherein the plant is a monocotyledonous or dicotyledonous plant and the compound is applied by post-emergent treatment of the sown areas or of the plants.
3. A method as claimed in claim 1 wherein the plant is a grass, cereal crop, tobacco, soya or an ornamental plant.
4. A method as claimed in claim 1 wherein the amount applied of the compound is between 0.1 and 5 kg of active compound per hectare, for the treatment of existing crops.

* * * * *